(12) United States Patent
Hwang

(10) Patent No.: US 10,457,451 B2
(45) Date of Patent: Oct. 29, 2019

(54) CLEANSING DEVICE

(71) Applicant: F.S.KOREA INDUSTRIES INC., Seoul (KR)

(72) Inventor: Jae Kwang Hwang, Seoul (KR)

(73) Assignee: F.S. KOREA INDUSTRIES INC., Seoul (KR)

( * ) Notice: Subject to any disclaimer, the term of this patent is extended or adjusted under 35 U.S.C. 154(b) by 59 days.

(21) Appl. No.: 15/538,635

(22) PCT Filed: Jan. 27, 2016

(86) PCT No.: PCT/KR2016/000871
§ 371 (c)(1),
(2) Date: Jun. 21, 2017

(87) PCT Pub. No.: WO2016/129830
PCT Pub. Date: Aug. 18, 2016

(65) Prior Publication Data
US 2017/0349340 A1    Dec. 7, 2017

(30) Foreign Application Priority Data

Feb. 9, 2015 (KR) .......................... 10-2015-0019717

(51) Int. Cl.
*B65D 47/42* (2006.01)
*A45D 34/04* (2006.01)
(Continued)

(52) U.S. Cl.
CPC .............. *B65D 47/42* (2013.01); *A45D 34/04* (2013.01); *A45D 34/042* (2013.01); *A45D 34/06* (2013.01);
(Continued)

(58) Field of Classification Search
CPC ...... B65D 47/42; B65D 47/12; B65D 47/043; B65D 51/24; B65D 77/30; A61Q 1/14;
(Continued)

(56) References Cited

U.S. PATENT DOCUMENTS 5,002,415 A * 3/1991 Gueret ................. A45D 40/265
401/119
6,334,727 B1 * 1/2002 Gueret ................... A45D 33/00
401/190

(Continued)

FOREIGN PATENT DOCUMENTS

JP   2001-258636 A    9/2001
JP   2001-286329 A   10/2001
(Continued)

*Primary Examiner* — Nicholas J. Weiss
(74) *Attorney, Agent, or Firm* — Heedong Chae; Lucem, PC

(57) ABSTRACT

Provided is a cleansing device which is configured to be used while being easily joined to a mineral water bottle to erase or adjust makeup by using mineral water conveniently even while going out and erase or adjust the makeup without a skin trouble by using the mineral water even in the case of traveling in an area where water is poor. The cleansing device includes: a first joining member joined to an opening of a mineral water bottle accommodating mineral water and including an applicator which allows mineral water accommodated in the mineral water bottle to be applied to a face of a user; and a second joining member detachably joined to the first joining member to protect the applicator of the first joining member.

4 Claims, 5 Drawing Sheets

(51) Int. Cl.
   *A47K 7/03*    (2006.01)
   *A61Q 1/14*    (2006.01)
   *B65D 47/04*   (2006.01)
   *B65D 47/12*   (2006.01)
   *B65D 77/30*   (2006.01)
   *A45D 34/06*   (2006.01)
   *B65D 51/24*   (2006.01)
   *A61K 8/96*    (2006.01)

(52) U.S. Cl.
   CPC ............. *A47K 7/03* (2013.01); *A61K 8/965* (2013.01); *A61Q 1/14* (2013.01); *B65D 47/043* (2013.01); *B65D 47/12* (2013.01); *B65D 51/24* (2013.01); *B65D 77/30* (2013.01); *A45D 2200/054* (2013.01); *A45D 2200/1009* (2013.01); *A45D 2200/1063* (2013.01); *A61K 2800/87* (2013.01)

(58) Field of Classification Search
   CPC ......... A61K 8/965; A47K 7/03; A45D 34/04; A45D 34/042; A45D 34/06; A45D 2200/1009; A45D 2200/1018; A45D 2200/1063
   See application file for complete search history.

(56) References Cited

U.S. PATENT DOCUMENTS

| | | | | |
|---|---|---|---|---|
| 6,755,585 B2 * | 6/2004 | Gueret | ............... | A45D 34/04 |
| | | | | 132/317 |
| 7,226,227 B2 * | 6/2007 | Gueret | ............... | A45D 34/06 |
| | | | | 132/317 |
| 7,845,871 B2 * | 12/2010 | Thiebaut | ............ | A45D 34/06 |
| | | | | 132/314 |
| 10,117,497 B1 * | 11/2018 | Murphy | ............. | A45D 34/00 |

FOREIGN PATENT DOCUMENTS

| JP | 2003-180448 A | 7/2003 |
| JP | 2008-539139 A | 11/2008 |
| KR | 10-1110692 B1 | 3/2012 |
| KR | 10-1478074 B1 | 1/2015 |

* cited by examiner

CLEANSING DEVICE

CROSS-REFERENCE TO RELATED APPLICATION

This application claims the benefit of Korean Application No. 10-2015-0019717 filed on Feb. 9, 2015 with the Korean Intellectual Property Office, the disclosure of which is incorporated herein by reference.

TECHNICAL FIELD

The present invention relates to a cleansing device, and more particularly, to a cleansing device which is configured to be used while being joined to a mineral water bottle to enable mineral water to be conveniently used without warring about a skin trouble when intending to erase or change make-up while going out or traveling.

BACKGROUND ART

In order to manage skin healthily, it is necessary to cleanly remove various wastes and pollutants present on the skin, and in particular, the following steps are carried out when erasing makeup which is color makeup.

In a first step, cosmetics are cleaned from the skin by using cleansing cream, in a second step, in a second step, pores are expanded using a steam-type towel, and in a third step, a face is washed using a soap or a cleansing foam. In addition, in a last fourth step, the pores are shrunk by using cold water or a cold towel to shrink the expanded pores.

Herein, when the face is washed in the third step, if water may be freely used in normal times, there is no problem, but while going out, the water cannot be used freely as at home, and as a result, the face cannot be normally washed and in this case, skin health may deteriorate due to the presence of the cosmetics.

In addition, when traveling on a foreign country, etc., if the face is washed to the erase make-up, a skin trouble may occur while washing the face in a country where water is poor.

PRIOR ART DOCUMENT

Patent Document (Patent Document 1) Korean Patent Unexamined Publication No. 10-2014-0137183

DISCLOSURE

Technical Problem

The present invention is proposed to solve the problem and an object of the present invention is to provide a cleansing device which is configured to be used while being easily joined to a mineral water bottle to erase or adjust makeup by using mineral water conveniently even while going out and erase or adjust the makeup without a skin trouble by using the mineral water even in the case of traveling in an area where water is poor.

Technical Solution

In order to achieve the object, a cleansing device according to an embodiment of the present invention, includes: a first joining member joined to an opening of a mineral water bottle accommodating mineral water and including an applicator which allows mineral water accommodated in the mineral water bottle to be applied to a face of a user; and a second joining member detachably joined to the first joining member to protect the applicator of the first joining member.

Preferably, a movement passage of the mineral water accommodated in the mineral water bottle is formed to penetrate at the center of the applicator.

Preferably, a seating groove in which a part of the applicator is inserted and seated is formed in the first joining member and a mineral water movement guide pipe is installed at the center of the seating groove, which is inserted into a part of the movement passage.

Preferably, a mineral water movement amount control member is installed in the mineral water movement guide pipe, which controls a movement amount of the mineral water accommodated in the mineral water bottle to a very small amount.

Preferably, a cross-cut mineral water through-hole is formed in the water movement amount control member.

Preferably, the second joining member includes a receiving groove in which a soap is received and a lid opening/closing the receiving groove.

Advantageous Effects

The aforementioned cleansing device is configured to be used while being easily joined to a mineral water bottle to erase or adjust makeup by using mineral water conveniently even while going out and erase or adjust the makeup without a skin trouble by using the mineral water even in the case of traveling in an area where water is poor.

MODE FOR INVENTION

Hereinafter, a preferable embodiment of the present invention will be described in detail with reference to the accompanying drawings.

Figure 1:
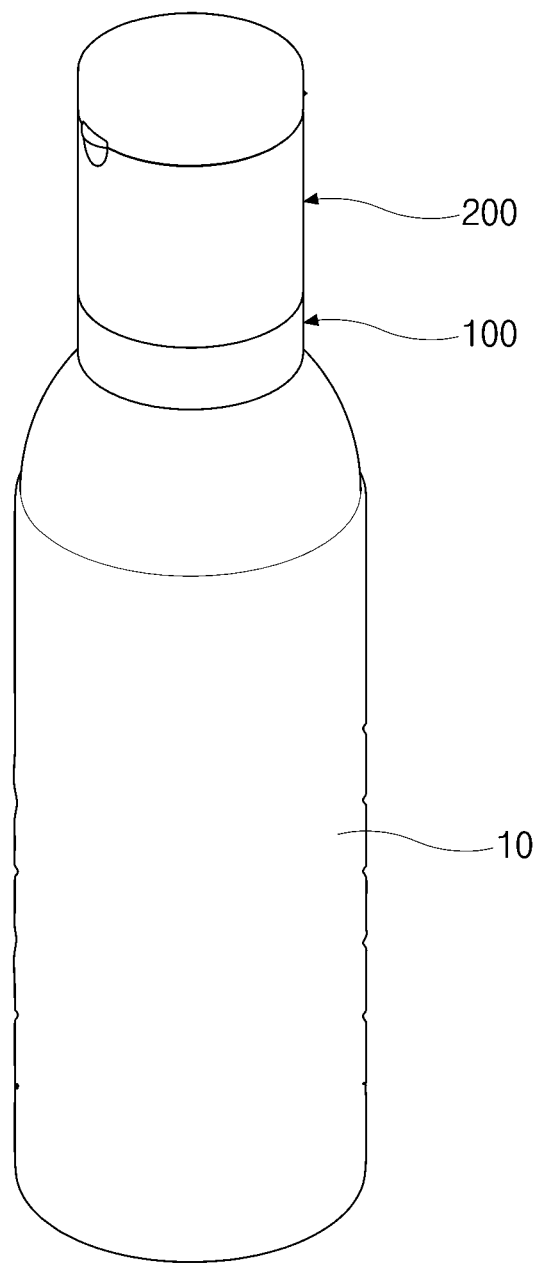
FIG. 1 is a diagram illustrating a state in which a cleansing device is joined to a mineral water bottle according to an embodiment of the present invention.
Figure 2:
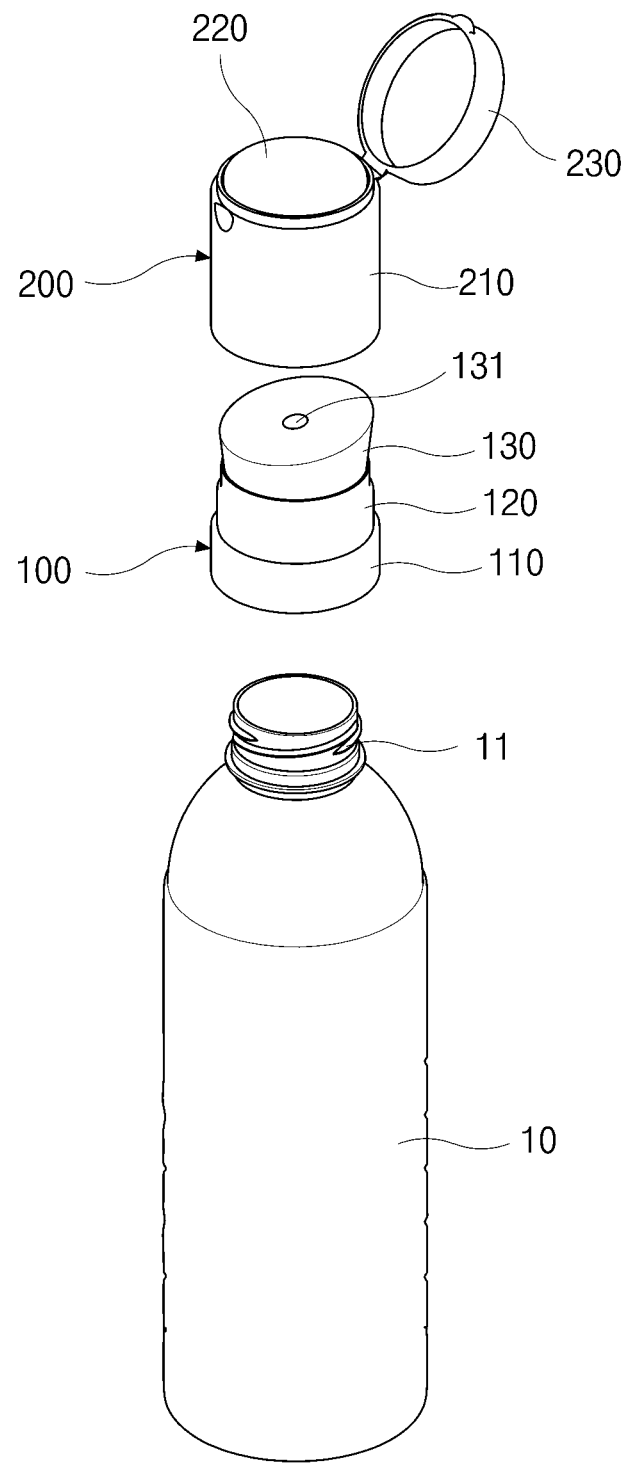
FIG. 2 is a diagram illustrating respective components constituting the cleansing device and the mineral water bottle according to the embodiment of the present invention.
Figure 3:
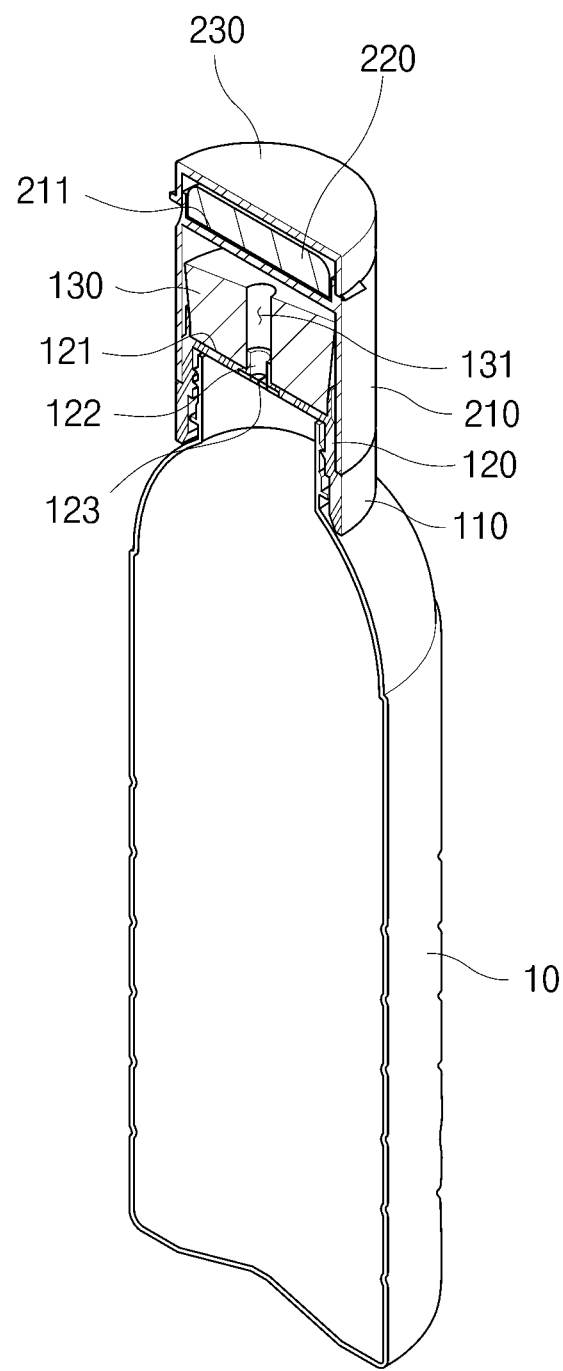
FIG. 3 is a cut-out view illustrating the state in which a cleansing device is joined to a mineral water bottle according to the embodiment of the present invention.
Figure 4:
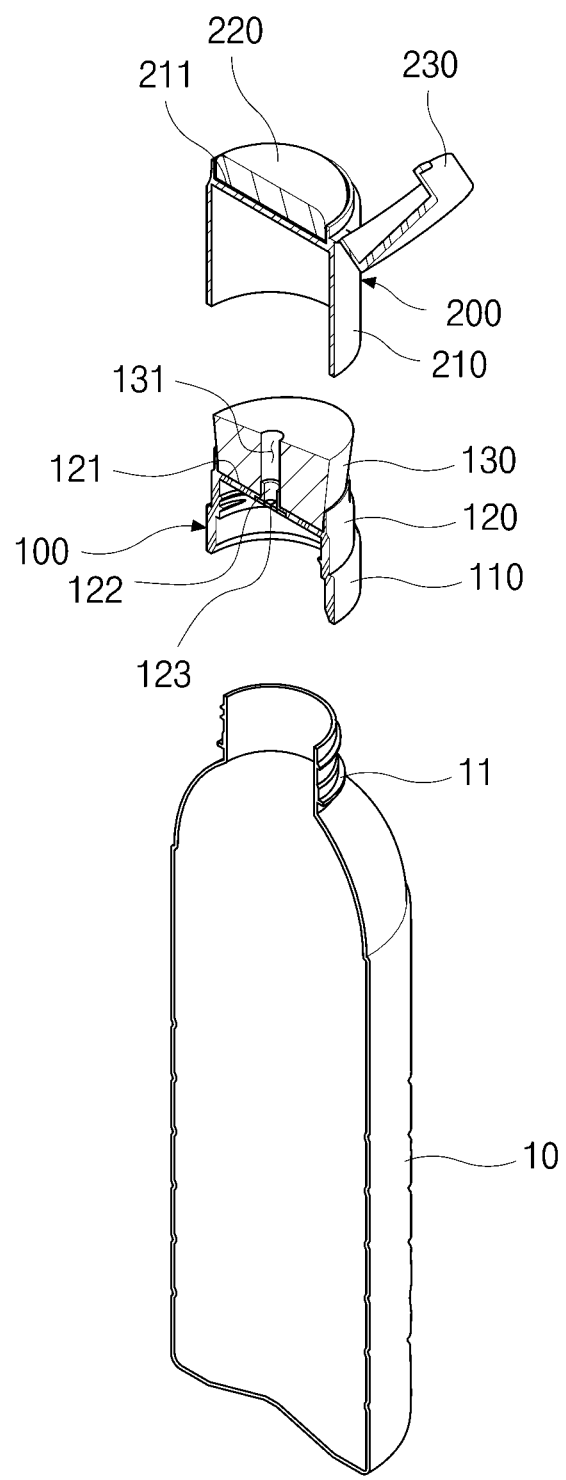
FIG. 4 is a cut-out view illustrating the respective components constituting the cleansing device and the mineral water bottle according to the embodiment of the present invention.
Figure 5:
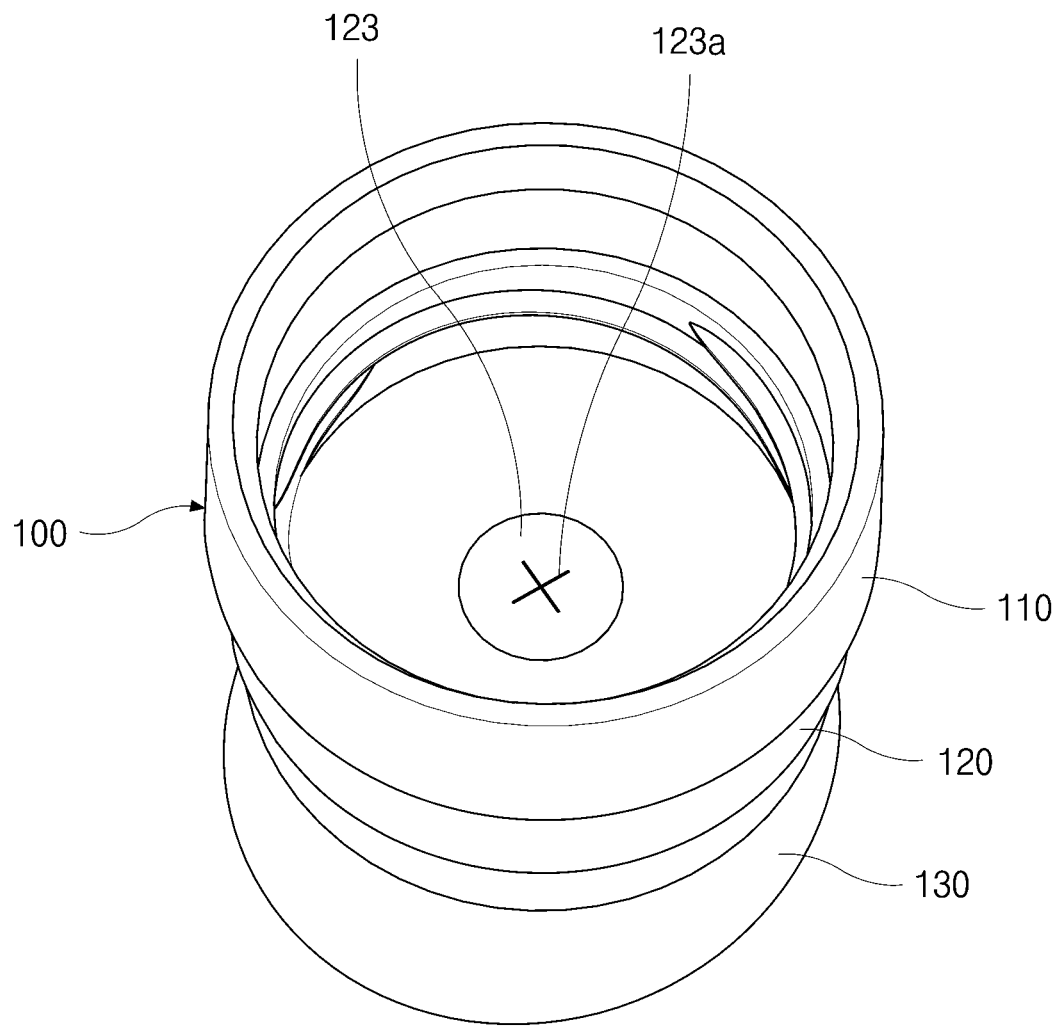
FIG. 5 is a diagram illustrating the cleansing device viewed from the bottom according to the embodiment of the present invention.

FIG. 1 is a diagram illustrating a state in which a cleansing device is joined to a mineral water bottle according to an embodiment of the present invention, FIG. 2 is a diagram illustrating respective components constituting the cleansing device and the mineral water bottle according to the embodiment of the present invention, FIG. 3 is a cut-out view illustrating the state in which a cleansing device is joined to a mineral water bottle according to the embodiment of the present invention, FIG. 4 is a cut-out view illustrating the respective components constituting the cleansing device and the mineral water bottle according to the embodiment of the present invention, and FIG. 5 is a diagram illustrating the cleansing device viewed from the bottom according to the embodiment of the present invention.

When described with reference to FIGS. 1 to 5, the cleansing device according to the embodiment of the present invention includes a first joining member 100 and a second joining member 200.

The first joining member 100 has a substantial cylindrical shape of which one side is opened, is joined to an opening 11 of a mineral water bottle 10 accommodating mineral water, and includes an applicator 130 that allows the mineral water accommodated in the mineral water bottle 10 to be applied to a face of a user.

The applicator 130 may be formed in a brush shape, but formed in various shapes which may be used in the face of the user like a puff shape.

Meanwhile, a movement passage 131 of the mineral water accommodated in the mineral water bottle 10 is formed to penetrate at the center of the applicator 130.

Meanwhile, a seating groove 121 having a size to insert and seat the applicator 130 only up to a partial height is formed in the first joining member 100 and a mineral water movement guide pipe 122 is installed at the center of the seating groove 121, which is inserted into a part of the movement passage 131 formed in the applicator 130.

A mineral water movement amount control member 123 is installed in the mineral water movement guide pipe 122, which controls a movement amount of the mineral water accommodated in the mineral water bottle 10 to a very small amount.

A cross-cut mineral water through-hole 123a is formed in the water movement amount control member 123 as illustrated in FIG. 3.

Meanwhile, the second joining member 200 includes a body 210 having the substantial cylindrical shape of which one side is opened, a receiving groove 211 provided to receive a soap on the top of the body, and a lid 230 opening/closing the receiving groove 211.

As the soap 220 is received, when the user intends to wash the face, the user need not carry a separate soap product, and as a result, a volume of a makeup article carried while going out or traveling may be reduced.

The aforementioned cleansing device is configured to be used while being easily joined to the mineral water bottle to erase or adjust the makeup by using the mineral water conveniently even while going out and erase or adjust the makeup without a skin trouble by using the mineral water even in the case of traveling in an area where water is poor.

While a specific embodiment of the present invention has been illustrated and described, it needs to be understood that various modifications and changes of the present invention can be made within the range without departing from the spirit and scope of the appended claims.

The invention claimed is:

1. A cleansing device comprising:
a first joining member joined to an opening of a mineral water bottle that accommodates mineral water, the first joining member includes an applicator which allows the mineral water accommodated in the mineral water bottle to be applied to a face of a user; and
a second joining member detachably joined to the first joining member to protect the applicator of the first joining member,
wherein a diameter of the first joining member is sized to engage the opening of the mineral water bottle,
wherein a movement passage of the mineral water accommodated in the mineral water bottle is formed to penetrate at and throughout a center of the applicator,
wherein a seating groove in which a part of the applicator is inserted and seated is formed in the first joining member and a mineral water movement guide pipe is installed at a center of the seating groove, which is inserted into a part of the movement passage, and
wherein a mineral water movement amount control member is installed in the mineral water movement guide pipe, which controls a movement amount of the mineral water accommodated in the mineral water bottle to a very small amount.

2. The cleansing device of claim 1, wherein a cross-cut mineral water through-hole is formed in the water movement amount control member.

3. The cleansing device of claim 2, wherein the second joining member includes a receiving groove in which a soap is received and a lid opening/closing the receiving groove.

4. The cleansing device of claim 1, wherein the second joining member includes a receiving groove in which a soap is received and a lid opening/closing the receiving groove.

* * * * *